(12) United States Patent
North

(10) Patent No.: US 8,527,054 B2
(45) Date of Patent: *Sep. 3, 2013

(54) IMPLANTABLE MEDICAL DEVICE CONNECTOR

(76) Inventor: Richard B. North, Baltimore, MD (US)

( * ) Notice: Subject to any disclaimer, the term of this patent is extended or adjusted under 35 U.S.C. 154(b) by 467 days.

This patent is subject to a terminal disclaimer.

(21) Appl. No.: 12/803,374

(22) Filed: Jun. 25, 2010

(65) Prior Publication Data

US 2010/0331924 A1 Dec. 30, 2010

Related U.S. Application Data

(60) Provisional application No. 61/221,953, filed on Jun. 30, 2009, provisional application No. 61/226,393, filed on Jul. 17, 2009.

(51) Int. Cl.
*A61N 1/375* (2006.01)

(52) U.S. Cl.
USPC ................................ 607/38; 607/36; 607/37

(58) Field of Classification Search
USPC ...................................... 607/36–38
See application file for complete search history.

(56) References Cited

U.S. PATENT DOCUMENTS

| | | | |
|---|---|---|---|
| 4,467,800 A | 8/1984 | Zytkovicz | |
| 5,304,219 A | 4/1994 | Chernoff et al. | |
| 5,383,913 A | 1/1995 | Schiff | |
| 5,383,914 A | 1/1995 | O'Phelan | |
| 5,470,346 A | 11/1995 | Adams | |
| 5,730,628 A | 3/1998 | Hawkins | |
| 5,782,892 A | 7/1998 | Castle et al. | |
| 5,843,141 A | 12/1998 | Bischoff et al. | |
| 6,198,969 B1 * | 3/2001 | Kuzma | 607/38 |
| 6,308,103 B1 | 10/2001 | Gielen | |
| 6,430,442 B1 | 8/2002 | Peters et al. | |
| 6,895,276 B2 | 5/2005 | Kast et al. | |
| 7,083,474 B1 | 8/2006 | Fleck et al. | |
| 7,239,916 B2 | 7/2007 | Thompson et al. | |
| 7,286,882 B2 | 10/2007 | Cole | |
| 7,425,142 B1 | 9/2008 | Putz | |
| 7,515,964 B1 | 4/2009 | Alexander et al. | |
| 7,563,141 B2 | 7/2009 | Alexander et al. | |
| 7,616,992 B2 | 11/2009 | Dennis et al. | |
| 7,641,520 B2 | 1/2010 | Marino | |
| 7,846,095 B2 | 12/2010 | Christopherson et al. | |
| 2003/0163171 A1 | 8/2003 | Kast et al. | |
| 2005/0027325 A1 | 2/2005 | Lahti et al. | |
| 2006/0167522 A1 | 7/2006 | Malinowski | |
| 2006/0172611 A1 | 8/2006 | Rodgers et al. | |
| 2007/0049985 A1 | 3/2007 | Kessler et al. | |
| 2007/0225772 A1 | 9/2007 | Lahti et al. | |
| 2007/0282385 A1 | 12/2007 | Rossing et al. | |
| 2008/0015668 A1 | 1/2008 | Soukup | |
| 2008/0154328 A1 | 6/2008 | Thompson et al. | |
| 2008/0246231 A1 | 10/2008 | Sjostedt et al. | |
| 2010/0114210 A1 | 5/2010 | Donofrio et al. | |
| 2010/0197174 A1 | 8/2010 | Lahti et al. | |

\* cited by examiner

*Primary Examiner* — Allen Porter, Jr.
(74) *Attorney, Agent, or Firm* — Whiteford, Taylor & Preston LLP

(57) ABSTRACT

Disclosed is an implantable medical device including a connector block that allows varied lead configurations to be used with a single connector block and implantable medical device assembly. The connector block is configured with one or more lead insertion lumens that are open at both ends, such that each end of the lead insertion lumen may receive a separate lead. The circuitry within the implantable medical device is configured to allow the delivery of electrical pulses from a pulse generator within the implantable medical device to two separate leads inserted within opposite ends of a single lead insertion lumen.

61 Claims, 6 Drawing Sheets

IMPLANTABLE MEDICAL DEVICE CONNECTOR

CROSS REFERENCE TO RELATED APPLICATION

This application is based upon and claims benefit of copending U.S. Provisional Patent Application Ser. No. 61/221,953 entitled "Implantable Medical Device Header or Connector for Connecting Leads to a Power Source", filed with the U.S. Patent and Trademark Office on Jun. 30, 2009 by the inventor herein; and is likewise based upon and claims benefit of copending U.S. Provisional Patent Application Ser. No. 61/226,393 entitled "Implantable Medical Device Header or Connector for Connecting Leads to a Power Source," filed with the U.S. Patent and Trademark Office on Jul. 17, 2009; both of which specifications are incorporated herein by reference.

FIELD OF THE INVENTION

The present invention relates generally to the field of implantable medical devices, such as electrical stimulators, defibrillators, and pacemakers, and more particularly to a connector assembly for such devices configured to couple leads to the implantable device.

BACKGROUND OF THE INVENTION

Implantable medical devices ("IMD") are used today for various applications to deliver electrical pulses from a pulse generator within the IMD, through an electrical lead connected to the IMD, to a targeted location within a patient's body. For instance, pacemakers are used to deliver electrical pulses generated within a pulse generator through an electrical lead to a patient's heart to maintain proper rhythm. In order to deliver those pulses, the electrical pulse from the generator is delivered through a lead connector assembly to a plurality of electrical contacts at one end of the lead, which lead then carries the electrical pulses to electrical contacts at the opposite end of the lead which are positioned adjacent the portion of the patient's heart that is to be stimulated.

Similarly, IMD's may be used in neurological applications, such as for deep-brain stimulation and spinal cord simulation, in which leads deliver electrical pulses generated in the IMD to targeted portions of a patient's brain or spinal cord.

In still other applications, leads may be used to sense particular conditions within a patient's body, and relay that sensed condition back to a processing unit within the IMD.

Many IMD's include a housing that houses the circuitry of the IMD, a connector block that connects the lead or leads to the IMD, and one or more leads inserted into the connector block to transfer electrical pulses generated within the IMD to the targeted portion of the patient's body. Many such connector blocks include female receptacles into which the male end of a multicontact lead may be inserted; however, the female receptacles are provided on only one end of the connector block. This configuration of the female receptacle of the header or connector may have a limiting effect on the number and types of leads that may be operated with a single implantable medical device. For instance, a connector block might have two receptacles, each providing 12 electrical contacts configured to receive a 12-contact lead. This configuration can be useful where the patient's condition requires the delivery of electrical stimulation using 12-contact leads, such as a 12-contact percutaneous electrode. If, however, the patient's condition changes such that an alternate configuration is desired (such as using 3 8-contact leads to more disparately apply the electrical pulses across a broader area), an alternative connector block must be provided that provides 3 8-contact receptacles. Requiring such a change of the IMD to receive an alternative lead configuration can be quite expensive and clearly uncomfortable and undesirable for the patient. Likewise, as doctors may have varied preferences for how and in what configuration electrical pulses should be delivered to a targeted portion of a patient's body (based on a particular patient's diagnosed condition), providing separate connector blocks for every possible configuration the doctor might come across can likewise become quite costly, as it significantly complicates the inventory that the doctor must maintain.

Therefore, it would be desirable to provide an improved connector block for an implantable medical device that could be variably configured to adapt to varied clinical conditions so as to allow the delivery of electrical pulses from an IMD in such varied clinical conditions using only a single, standard connector block.

Moreover, in some operative environments, operative space may be limited for inserting a lead longitudinally into the connector block on the IMD. In such environments, it would be desirable to provide an improved connector block that could allow insertion of leads into the connector block without requiring their longitudinal insertion, and that was otherwise configurable to minimize the amount of space that must be available in the operative environment to engage the leads with the connector block assembly.

SUMMARY OF THE INVENTION

Disclosed is an IMD including a connector block that allows varied lead configurations to be used with a single connector block and IMD assembly. The connector block is configured with one or more lead insertion lumens that are open at both ends, such that each end of the lead insertion lumen may receive a separate lead. The circuitry within the IMD is configured to allow the delivery of electrical pulses from a pulse generator within the IMD to two separate leads inserted within opposite ends of a single lead insertion lumen.

With regard to an aspect of a particularly preferred embodiment of the invention, a connector assembly for removably attaching a plurality of leads to an implantable medical device is disclosed, comprising a connector block housing having a first end and a second end, the connector block housing further comprising a lower casing and an upper casing removably attached to the lower casing, and at least one lead insertion lumen extending through the connector block housing from the first end to the second end and providing two points of entry through the connector block housing and into the lead insertion lumen, the lead insertion lumen further comprising a plurality of electrical contacts disposed within the lead insertion lumen and configured to direct an electrical pulse from a pulse generator assembly to a lead positioned within the lead insertion lumen.

BRIEF DESCRIPTION OF THE DRAWINGS

The numerous advantages of the present invention may be better understood by those skilled in the art by reference to the accompanying drawings in which.

DETAILED DESCRIPTION OF THE INVENTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

An IMD is described herein, such as an implantable pulse generator, which includes a connector block that allows varied lead configurations to be used with a single connector block and IMD assembly. The connector block has one or more insertion lumens extending through the connector block, providing two insert openings into which two separate leads may be inserted to separately receive electrical pulses from a pulse generator within the IMD. The pulse generator is preferably configurable so as to allow the delivery of appropriate pulses to the appropriate electrical contacts within the insertion lumen, thus allowing the intended stimulation signal to be transmitted through the intended leads and out to the stimulating contacts at the end of each such lead. Such configuration allows for varied lead configurations to be used with a single IMD, thus minimizing the need to maintain large inventories of varied connector block configurations and minimizing the extent of invasion into a patient's body if lead modifications must be made after the IMD has been implanted.

Figure 1:
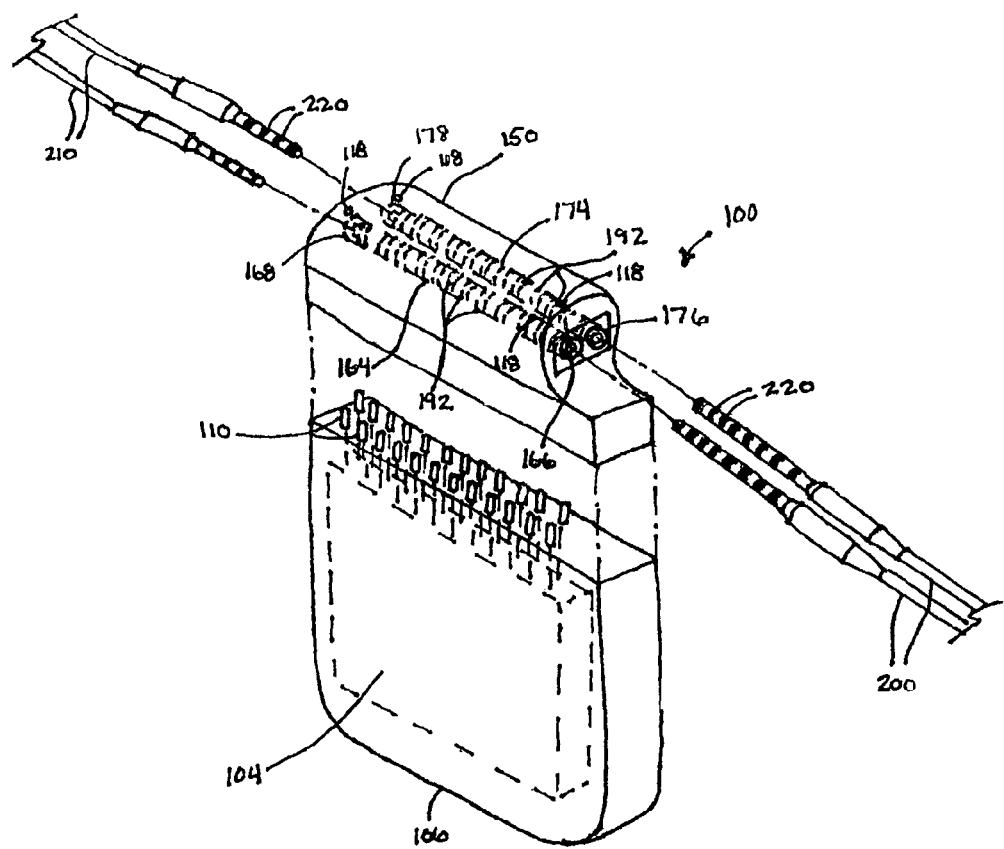
FIG. 1 is an exploded perspective view of an implantable medical device in accordance with an exemplary embodiment of the present invention.

As shown generally in the exploded perspective view of FIG. 1, an exemplary embodiment of a biologically inert IMD 100 is shown including a pulse generator assembly 104 and a connector block 150 according to certain aspects of the present invention. In exemplary embodiments, connector block 150 receives the insertion ends of one or more leads 200 and 210, thereby electrically connecting leads 200 and 210 with pulse generator assembly 104, and in turn allowing an electrical pulse to pass from pulse generator assembly 104 to an electrode, a contact pad, or another connector in series, connected to the opposite end of each of the leads.

While FIG. 1 particularly shows a connector block 150 in the form of a header which is joined to the body of a pulse generator, those of ordinary skill in the art will recognize that this illustrates only one possible configuration of the invention. Alternatively, a connector block embodying the invention could be joined to the end of an extension cable or lead(s), remote from the pulse generator. Any number of such connectors could be assembled in series, and by the variety of assembly arrangements which are possible, they could reconfigure or remap subsets of contacts and/or leads.

In the current embodiment, connector block 150 includes two insertion lumens 164 and 174 configured to receive leads 200 and 210 within either or, simultaneously, both open ends of a single insertion lumen. Insertion lumens 164 and 174 are configured to receive and removably hold the insertion ends of electrical leads 200 and 210 in a conventional manner, such as (by way of non-limiting example) a bal seal providing a physical and electrical connection to the multiple electrical contacts within each of insertion lumens 164 and 174 through a compressive contact, as are known to those of ordinary skill in the art. Those of ordinary skill in the art will also readily recognize that other mechanisms may likewise be used to mechanically hold leads 200 and 210 within insertion lumens 164 and 174 without departing from the spirit and scope of the instant invention, such as variously configured resilient, compression fit mechanisms, various snap-fit connection mechanisms, friction fit mechanisms, threaded connection mechanisms, and the like. As shown in the exemplary embodiment of FIGS. 1-3, a plurality of set screws 118 are provided to engage with the inserted end of the leads once they are positioned within the insertion lumens. Alternative secondary connector mechanisms that assist to ensure the secure connection of the lead within the insertion lumen may also be employed. For instance, various types of set pins and/or O-ring mechanisms may be employed.

Likewise, while only two insertion lumens are shown in the exemplary embodiment of FIG. 1, those of ordinary skill in the art will recognize that more or fewer insertion lumens may be provided in a connector block 150 without departing from the spirit and scope of the instant invention.

In the exemplary embodiment of FIG. 1, each of insertion lumen 164 and insertion lumen 174 is provided first and second openings in connector block 150 configured to receive the proximal end of a lead, such as leads 200 and 210. More particularly, the first insertion lumen 164 is provided a first opening 166 and a second opening 168, with insertion lumen 164 extending through connector block 150 between first opening 166 and second opening 168. Similarly, the second insertion lumen 174 is provided a first opening 176 and a second opening 178, with insertion lumen 174 extending through connector block 150 between first opening 176 and second opening 178. The first and second openings of the first and second insertion lumens may be variously sized and may be positioned at various locations within connector block 150. Thus, each of the insertion lumens includes an open first end and an open second end, thereby establishing two open-ended insertion lumens within the body of the connector block 150.

As shown in the exemplary embodiment of FIG. 1, each of connection lumens 164 and 174 extends the length and through the interior of connector block 150. In the current embodiment, disposed along each of connection lumens 164 and 174 are a plurality of electrical contacts 192. In the exemplary embodiment of FIG. 1, each of first and second connection lumens 164 and 174 contain 12 electrical contacts. In an alternative preferred embodiment, each connection lumen may include 24 contacts. As will be apparent to those of ordinary skill in the art, the number of contacts disposed in a connection lumen may vary from the foregoing as required for a particular application without departing from the spirit and scope of the invention. The configuration and dimensional characteristics of the electrical contacts within each connection lumen may vary to accommodate various technologies known to those skilled in the art.

In the exemplary embodiment of FIG. 1, connector block 150 is hermetically sealed to a housing 106, which housing in turn contains pulse generator assembly 104. The plurality of contacts 192 connect with circuitry of the pulse generator assembly 104 allowing the electrical stimulation to pass through to the plurality of contacts 192. More particularly, pulse generator 104 preferably includes a power source and electronic circuitry configured to transmit electrical pulses to, for example, a plurality of pins 110 or other similarly configured electrical conductors capable of transmitting an electrical pulse to contacts 192 in the connection lumens. One end of pins 110 may connect with the electronic circuitry of pulse generator 104 in a manner that allows it to receive electrical pulses from the power source. The opposite end of pins 110 may allow for the transfer of electrical energy from the pulse generator assembly 104 to the contacts 192 within the insertion lumens. Further, the power source may include various types and configurations of batteries, various configurations of super-capacitors and such other power source technology that is known to those skilled in the art for producing an electrical impulse. In an exemplary embodiment, the power source employs a rechargeable or replenishable power source, such as a rechargeable battery or other replenishable power device. The particular type and configuration of the power source may vary as contemplated by those skilled in the art without departing from the scope and spirit of the current invention.

Those of ordinary skill in the art will also recognize that a wide variety of configurations may be used to electrically transmit electrical pulses from pulse generator 104 to electrical contacts 192 without departing from the spirit and scope of the invention, including (in the case where connector block 150 is not joined directly to pulse generator assembly 104) electrical cables or leads extending from pins 110, or alternatively directly attaching to generator assembly 104, that transmit the electrical pulses to a remotely located connector block 150. Further, the connector block 150 may include an electrical connector plate that contacts the circuitry on one side and the contacts of the channel on the other side. It is further contemplated that the components may provide for or assist with the connection of the connector block 150 with the housing 106. The use of various mechanisms that would further promote any of the above described features of the current invention and allow the implementation of the implantable medical device 100 in a manner similar to that described herein are contemplated for use. Further, as a variety of configurations are readily available and known to those of ordinary skill in the art for electrically communicating a pulse generator with electrical contacts within a connection lumen (such as those set forth in U.S. Patent Application Publication No. 2006/0167522, the specification of which is herein incorporated by reference), such assembly is not further detailed here.

The electronic circuitry of pulse generator 104 may preferably include a circuit board coupled to the power source and including various electronic components, which may include but are not limited to power circuits and a microcontroller. Such microcontroller is preferably capable of directing electrical pulses to specific pins 192 within each of connection lumen 164 and connection lumen 174, and is likewise programmable (such as by way of a remote, handheld programmer communicating with telemetry circuitry in pulse generator 104) so as to store particular electrical pulse generation profiles for use depending on the lead configuration that is to be used with the IMD. Thus, by way of non-limiting example, in the case where a single 12-contact lead is to be used, the microcontroller of pulse generator 104 may be programmed to deliver electrical pulses appropriate for each of the contacts on such 12-contact lead. Likewise, where both an 8-contact lead and a 4-contact lead are to be used (each being inserted into an opposite end of the particular connection lumen), the microcontroller of pulse generator 104 may be programmed to deliver a first set of electrical pulses appropriate for the contacts of the 8-contact lead to eight of the contacts within the connection lumen, and to deliver a second set of electrical pulses appropriate for the contacts of the 4-contact lead to four of the contacts within the same connection lumen. Those of ordinary skill in the art will recognize that various other electrical pulse generation profiles may be desired for various patient conditions.

It is to be understood that connector block 150 described herein is exemplary and that various components, dimensional characteristics and/or configurations may be modified and still fall within the scope of the current invention. For instance, alternative embodiments may include a connector block with one insertion lumen or three or more insertion lumens disposed within the casing.

It is further contemplated that one or both ends of an insertion lumen may not have a lead inserted within it. Stops or plugs, such as plastic blanks, may be inserted into the opening of the unused end. Such plugs may be sized to complement, and facilitate precise insertion of, the lead. For example, a 12-contact insertion lumen may be provided with a plug at one end whose length occupies 4 contact positions, such that when an 8-contact lead is inserted so as to stop against the plug, it is at the correct depth. Alternatively, the length of the plug might occupy zero contacts, occluding only the end of the port, such as might be desirable for use with a 12-contact lead.

The insertion end of the leads are inserted through the insert openings of the insertion lumens in order to place contacts 220 on leads 200 and 210 in electrical communication with electrical contacts 192 within the insertion lumen. Overall, the configuration and dimensional characteristics of the insertion lumens can be varied as may be contemplated by those skilled in the art without departing from the spirit and scope of the current invention.

It is further contemplated that a connector block 150 may include two or more insertion lumens that are differently configured from one another. For example, the dimensional characteristics between the insertion lumens may vary. The number and configuration of electrical contacts within the insertion lumens may also vary. It is further contemplated that the connector block 150 may include, for instance, three insertion lumens where one of the insertion lumens is an open-ended insertion lumen as described above, and the other two insertion lumens include a closed second end.

The varying configurations available for the insertion lumens of the current invention allow leads of various configurations to be received and operationally coupled with a pulse generator assembly to transmit electrical stimulation provided by the implantable medical device to a desired portion of a patient's body. In the exemplary embodiment, and as particularly shown in FIG. 1, first leads 200 include an insertion end having a plurality of contacts 220. Likewise, second leads 210 include an insertion end having a plurality of contacts 220. By way of non-limiting example, there may be 8 contacts located on each of first leads 200, and 4 contacts located on each of second leads 210. In alternative embodiments, any of the leads may include 12 contacts, 8 contacts or various other numbers of contacts as may be required for a particular application.

Those of ordinary skill in the art will recognize that in some instances, particular applications may warrant the use of four separate leads, which would correspond to the use of (again by way of non-limiting example) a 4×6 configuration (in which 4 leads are used, each having 6 electrical contacts) or, alternatively, a 2×4 configuration in combination with a 2×8 configuration (in which 4 leads are used, 2 having 4 electrical contacts and 2 having 8 electrical contacts). In order to simplify inventory, a lead manufacturer may desire to provide only 8-contact leads, in which case the connector block 150 may be configured to allow partial insertion (i.e., leaving two or four contacts exposed outside of connector block 150) if only 6 or 4 contacts are to be used. The order and number of the contacts at pulse generator 104 may, in turn, be programmed as detailed above to provide for such connection, such that the tip contact at the insertion end of the lead corresponds to the appropriate electrical contact 192 within the insertion lumen.

Figure 2:
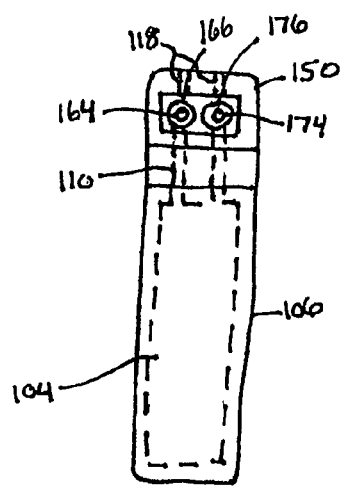
FIG. 2 is a front view of the implantable medical device of FIG. 1.
Figure 3:
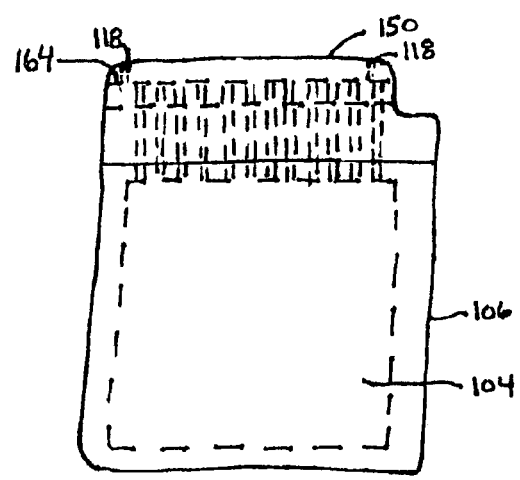
FIG. 3 is a side view of the implantable medical device of FIG. 1.

It may also be desirable in certain applications to provide for insertion of a lead into connector block 150 at varying depths so as to accommodate different lead designs by different manufacturers, again configuring the electrical contacts 192 within the respective insertion lumens to correspond to the appropriate contacts on such lead. As shown in FIGS. 1-3, set screws 118 may be provided at both ends of each of insertion lumens 164 and 174 to assist in holding such leads in place after insertion, whether partial or whole, into the respective insertion lumen.

Each of the insertion ends of leads 200 and 210 are inserted into the insert openings of the first or second ends of the first and second insertion lumens, respectively. As described above, the leads may be inserted simultaneously into both ends of a single insertion lumen. Once the insertion ends of leads 200 and 210 are fully inserted into their respective insertion lumens, the plurality of electrical contacts on those insertion ends of leads 200 and 210 are positioned in electrical communication with the plurality of contacts 192 contained within the respective insertion lumen. In the exemplary embodiment shown in FIGS. 1-3, the connector block 150 allows the simultaneous connection of four leads with the implantable medical device 100, thereby further allowing electrical stimulation to be provided to all four leads simultaneously.

In an exemplary embodiment, the end of the lead opposite the insertion end can terminate in varying configurations, such as an in-line electrode or contact paddle that provides varying configurations of contacts for direct application of the electrical stimulation to a desired location, such as a particular location on or in a patient's body. In one embodiment, the contacts may be provided on a paddle in, for example, a 3×8 configuration (the 3×8 configuration is in reference to the number of columns and rows of individual contacts provided on the paddle). In this embodiment, the 24 contacts may be wired to two 12-contact insertion ends, which connect to two 12-contact insertion lumens on the connector block 150. In a contemplated alternative embodiment, the contacts may be provided on three separate leads, each of which may be inserted and connected with connector block 150 independently; these may, by way of non-limiting example, be connected to the same two 12-contact insertion lumens by inserting two 4-contact leads (which may terminate in an 8-contact female connector) into one end of the two channels so as to accommodate one 8-contact lead extending from the paddle, while the other two leads are inserted into the other end of the two insertion lumens.

By way of further example, the configuration of the contacts on a paddle may alternatively be 4×6, or any other variety of electrode configurations. Still further, the contacts may alternatively comprise an in-line percutaneous electrode similar to a wire, wherein the conductive section extends in an integral manner from the rest of the lead. Various other configurations as contemplated by those of ordinary skill in the art may be employed without departing from the scope and spirit of the present invention.

Figure 4:
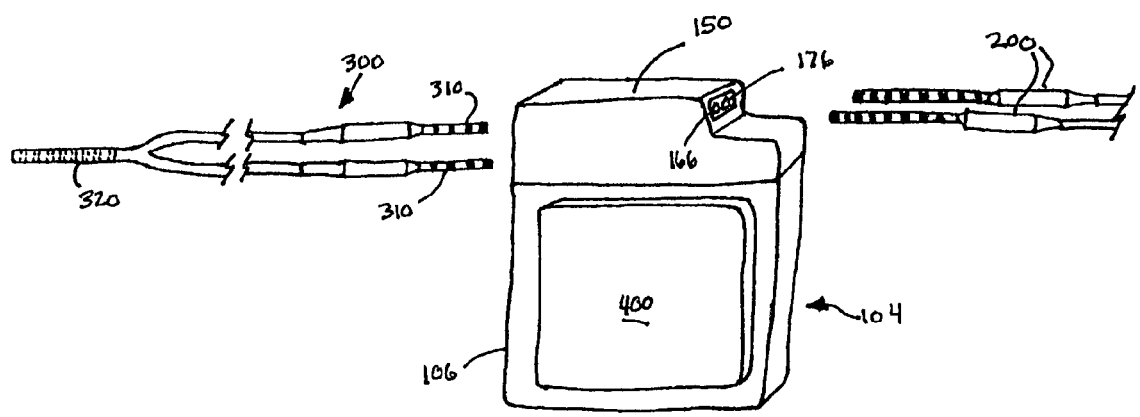
FIG. 4 is a perspective view of an application of the implantable medical device of FIG. 1.

Next, and with particularly reference to FIG. 4, so as to accommodate a variety of leads with different numbers of contacts and varying contact pad or in-line percutaneous electrode designs and configurations, adapters may be used with the current invention. For example, a "Y" cable adapter may be used having, for instance, an 8-contact male end and two 4-contact female ends, in which case the 8-contact male end may be inserted into one end of a single insertion lumen, with pulse generator 104 being programmed to deliver electrical pulses to the appropriate contacts on the 8-contact male end so as to transmit the intended electrical pulses to the separate 4-contact female ends, which in turn may separately transmit the received electrical pulses on to additional leads and/or connector blocks attached to the 4-contact female ends. Alternatively, and with regard to a particular aspect of the invention as shown in FIG. 4, a "Y" cable adapter 300 may be configured with two 4-contact male ends 310 which may be inserted into each of two insertion lumens of connector block 150, while the opposite end of the "Y" cable adapter may terminate in an 8-contact female receptacle 320 configured to receive an 8-contact insertion end of a lead. In this novel configuration, the IMD could simultaneously support a total of three 8-contact percutaneous leads, which percutaneous leads could then be placed side-by-side to provide a minimally invasive tripole. Those of ordinary skill in the art will also recognize, however, that the adapter may include various numbers of contacts on either end without departing from the spirit and scope of the invention. In particularly preferred embodiments, the adapter 300 may be either rigid or semi-rigid, may be integrated tightly into the connector block 150, or alternatively may be integrated with the outer body of pulse generator assembly 104, such as by being coiled around a reel attached to the outer body of pulse generator assembly 104, or removably housed within a shield or a bag 400 (FIG. 4) attached to one side of the outer body of pulse generator assembly 104 within which redundant lead may be coiled. The operational use and connection scheme of the adapters may vary as contemplated by those skilled in the art and may allow any number of leads to be connected to a power source (described below) of the IMD 100 of the current invention.

In the exemplary embodiment shown in FIGS. 1-3, the pulse generator assembly 104 includes a housing 106, otherwise commonly referred to as a "casing" or "can". In one embodiment, the housing 106 may be integrally formed with the connector block 150. Alternatively, connector block 150 may be connected with the housing 106 in a manner that allows the removal of the connector block 150. Thus, similarly or differently configured housings 106 and connector blocks 150 may be interconnected with one another and fall within the scope of the current invention so long as at least one insertion lumen open at both ends is included within the connector block. Thus, the current invention contemplates that the configuration of the IMD 100 may be varied without departing from the spirit and scope of the invention.

Various connection mechanism(s) as contemplated by those skilled in the art may be employed by the current invention to allow the interchangeability of the housing 106 and connector block 150. For example, a compression lock assembly may be employed where the connector block 150 may include a compressive device or receiver that connects with a receiver or compressive device included on the housing 106. Other connection mechanisms, such as a snap-fit, friction-fit or otherwise known to those skilled in the art may likewise be employed by the current invention. Thus, it is contemplated that the positioning of the various components of the various connection mechanisms used to attach the connector block 150 to the housing 106 will be complimentary to one another.

Figure 5:
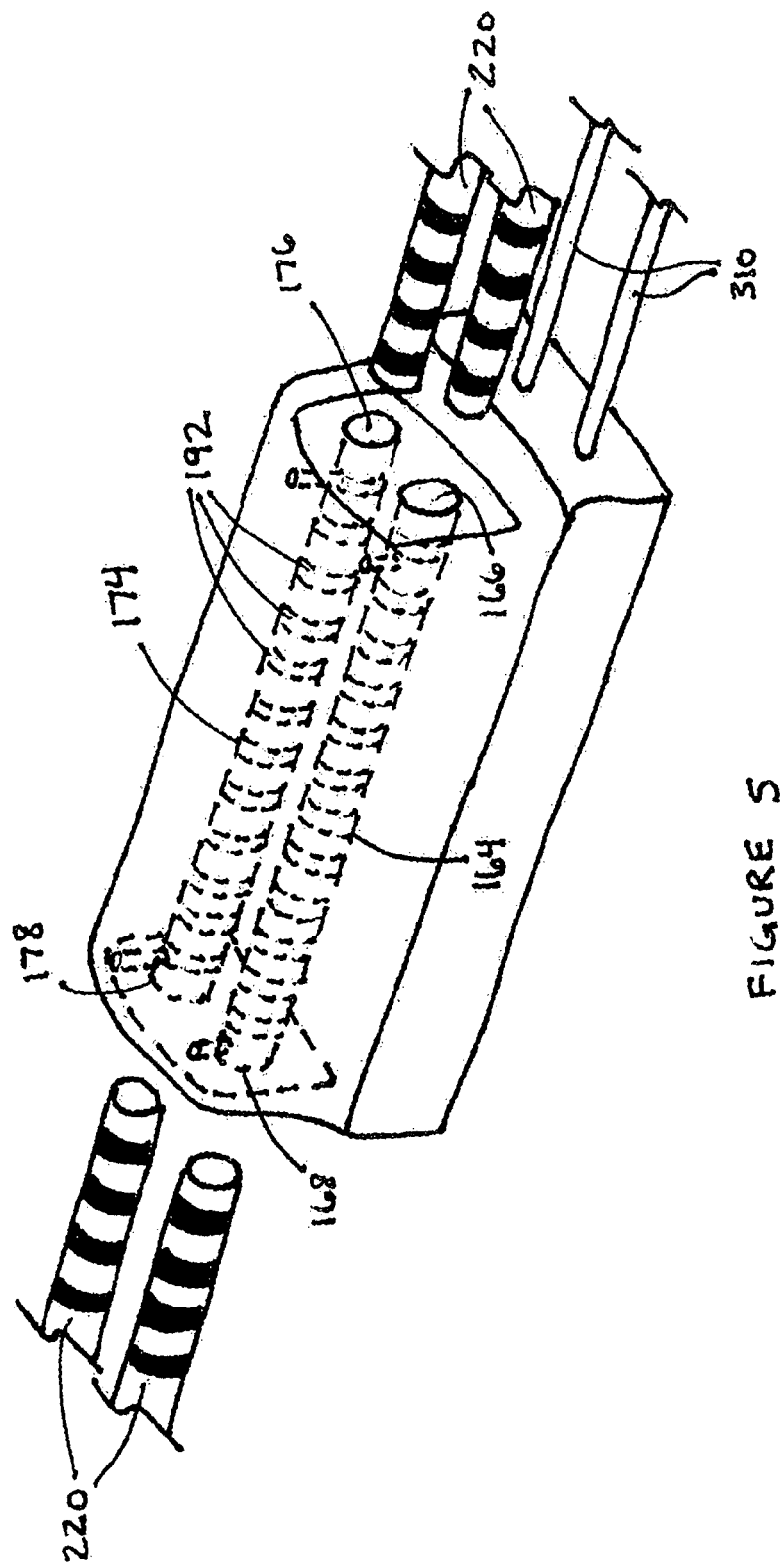
FIG. 5 is a perspective view of a connector block according to one embodiment of the invention.

Likewise, as shown in FIG. 5, connector block 150 may be provided as an entirely separate structure from a housing 106 and connected thereto via one or more electrical cables 310. In this case, electrical cables 310 in one embodiment may provide an extended electrical connection between pulse generator assembly 104 within housing 106, and contacts 192 in insertion lumens 164 and 174, in which case electrical cables 310 may be directed into housing 106 to directly engage pulse generator assembly 104. Alternatively, electrical cables 310 may terminate in leads configured for insertion into insertion lumens on an IMD header of traditional configuration.

Figure 6:
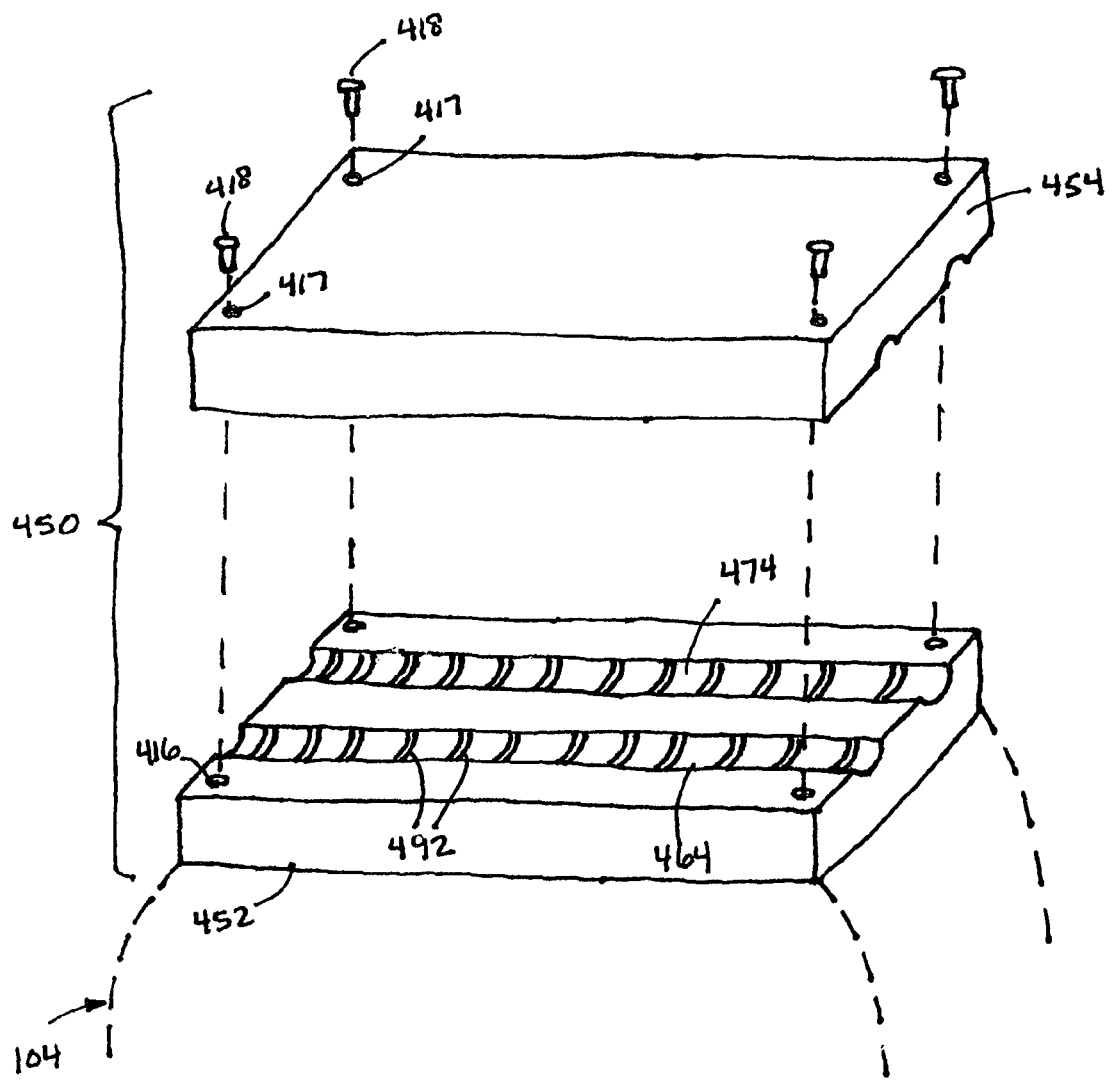
FIG. 6 is an exploded, perspective view of an implantable medical device having a modular connector block.

With regard to an embodiment of the invention, and with particular reference to FIG. 6, a connector block 450 may alternatively be formed in a modular assembly including a lower casing 452 having a first insertion lumen 464 and a second insertion lumen 474 extending through casing 452, wherein each of first insertion lumen 464 and second insertion lumen 474 have a plurality of electrical contacts 492 that again connect with circuitry of the pulse generator assembly 104 allowing the electrical stimulation to pass through to the plurality of electrical contacts 492, all as described in greater detail above. However, each of first insertion lumen 464 and second insertion lumen 474 are formed as preferably half cylinders having an open top, thus allowing a lead to be laid or pressed down into the desired insertion lumen instead of requiring a longitudinal insertion of the lead into the insertion lumen. By allowing the lead to be so laid down into the channels formed by each of insertion lumen 464 and insertion lumen 474, the operator may visually align the contacts 220 on a lead with the electrical contacts 492 in order to obtain the desired alignment (i.e., the desired longitudinal position of the lead 200 or 210 within the associated insertion lumen 464 or 474) without requiring the operator to guess as to alignment or to use a stop inserted in the opposite end of the respective insertion lumen. Once the operator has so laid the lead or leads in the desired insertion lumens 464 and/or 474, an upper casing 454 may be placed on top of and tightly joined to lower casing 452 to seal the casings together, forming a closed, complete connector block 450. Upper casing 454 may be configured as a cap, lid, membrane, or adhesive layer that seals and completes connector block 450. Upper casing 454 may be joined to lower casing 452 in various manners to provide a completely sealed, biologically inert connector block 450. For instance, and by way of non-limiting example, one or more threaded connectors 418 (e.g., a screw or bolt) may be inserted though one or more openings 417 in upper casing 454 and into threaded receivers 417 on lower casing 464 in order to removably attach upper casing 454 to lower casing 452. Of course, those of ordinary skill in the art will recognize that other connector devices, such as compression locking mechanisms or friction fit locking mechanisms, may be used without departing from the spirit and scope of the invention.

Optionally, modular connector block 450 may include an adapter 500 configured to allow all leads that an operator desires to connect to a single pulse generator assembly 104 to extend from the connector block 450 in a single direction, rather than from opposite ends of the connector block 450. Adapter 500 may including a casing 562 having a lead insertion lumen 564 extending therethrough (of similar configuration to lead insertion lumens 464 and 474). Lead insertion lumen 564 may, in turn, be provided a first set of electrical contacts 569 and a second set of electrical contacts 570, each of which are configured to deliver an electrical pulse to a lead positioned within insertion lumen 564. In order to electrically interconnect such electrical contacts 569 and 570 with the circuitry of pulse generator assembly 104, each of the sets of electrical contacts 569 and 570 are in electrical communication with a lead connector assembly 510 comprising a first lead segment 510A and a second lead segment 510B of substantially identical configuration. One end of first lead segment 510A is preferably in the form of a traditional electrical lead, having a plurality of contacts 513 situated along the terminating length of lead segment 510A. The opposite end of first lead segment 510A extends into casing 562, and in turn establishes an electrical connection between contacts 513 and the first set of electrical contacts 569 in insertion lumen 564 via electrical conductors 514. Similarly, one end of second lead segment 510B is preferably in the form of a traditional electrical lead, having a plurality of contacts 517 situated along the terminating length of lead segment 510B. The opposite end of second lead segment 510B extends into casing 562, and in turn establishes an electrical connection between contacts 517 and the second set of electrical contacts 570 in insertion lumen 564 via electrical conductors 518. Each of lead segments 510A and 510B are configured for insertion into insertion lumens 464 and 474 of lower casing 452, such that the contacts 513 and 517 of lead segments 510A and 510B, respectively, may be placed in contact with electrical contacts 492 of insertion lumens 464 and 474. As a result, when pulse generator assembly 104 supplies an electrical pulse to the corresponding contacts 492 in insertion lumens 464 and 474, that electrical pulse is in turn passed to lead segments 510A and 510B, and on to contacts 569 and 570 within insertion lumen 564 of adapter 500. Those electrical pulses may, in turn, then be transferred to a lead positioned within insertion lumen 564. With this configuration, if an operator wishes to deploy multiple leads, two of which have a number of contacts 220 less than the number of electrical contacts 492 in insertion lumens 464 and 474, those leads may be placed in insertion lumens 464 and 474, and the remaining electrical contacts 492 may be used to supply a third lead positioned in insertion lumen 564 in adapter 500, thus allowing all of such leads to extend in the same direction from connector block 450. This configuration may make removal, insertion, lead adjustment and/or replacement easier for a user of the device.

Figure 8:
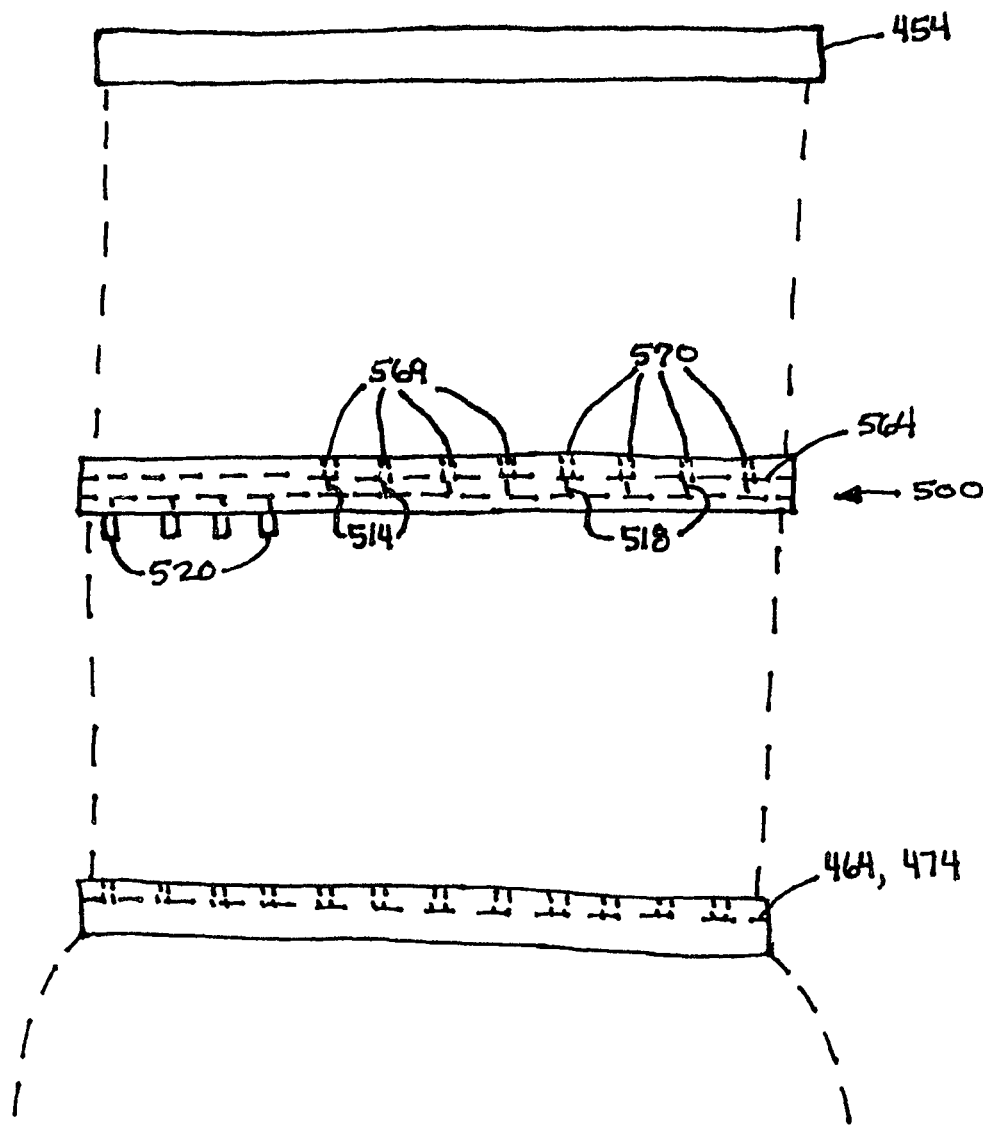
FIG. 8 is an exploded, side view of an implantable medical device having a modular connector block and an adapter within the connector block.

Alternatively, instead of electrically connecting electrical contacts 569 and 570 of insertion lumen 564 with electrical contacts 492 of insertion lumens 464 and 474 through the use of external lead segments 510A and 510B, direct, internal connections may optionally be provided. In this configuration, and with reference to FIG. 8, two rows of contacts 520 may extend outward from the bottom of adapter 500 and are preferably configured to sit within insertion lumens 464 and 474 of lower segment 452 of connector block 450 where they may be placed in electrical communication with electrical contacts 492. Within adapter 500, one row of contacts 520 is in electrical communication with the first set of electrical contacts 569 in insertion lumen 564 via electrical conductors 514, while the other row of contacts 520 is in electrical communication with the second set of electrical contacts 570 in insertion lumen 564 via electrical conductors 518. By providing such internally situated contacts 520, the use of extraneous cabling associated with lead segments 510A and 510B may optionally be avoided, providing a more compact and potentially more easily manufactured connector block 450.

Figure 7:
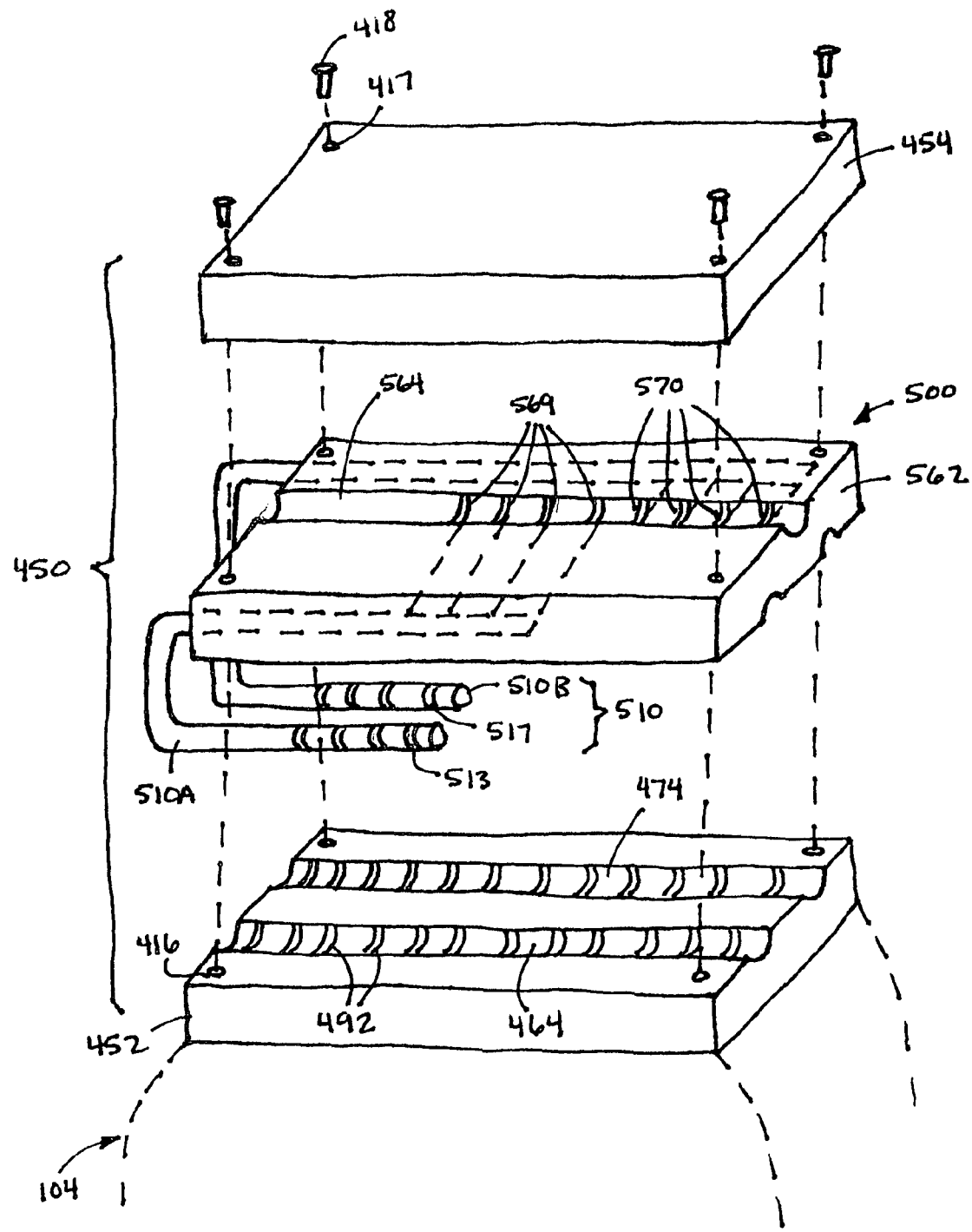
FIG. 7 is an exploded, perspective view of an implantable medical device having a modular connector block and an adapter within the connector block.

As yet another alternative, while FIG. 7 particularly shows adapter 500 configured as a separate layer sandwiched between lower casing 452 and upper casing 454, those of ordinary skill in the art will recognize that first casing 452 could alternatively be configured with a third insertion lumen extending parallel to insertion lumens 464 and 474 and having internal electrical contacts wired in parallel with electrical contacts 492 in each of insertion lumens 464 and 474. More particularly, one half of the electrical contacts in the third insertion lumen may be wired in parallel with four electrical contacts 492 in insertion lumen 464, while the remaining half of the electrical contacts in the third insertion lumen may be wired in parallel with four electrical contacts 492 in insertion lumen 474. Preferably, those contacts in insertion lumens 464 and 474 that are so wired to the electrical contacts in the third insertion lumen are contacts positioned at an end of each of the respective insertion lumens. In this case, and with regard to the particular exemplary configuration shown in FIG. 7, connector block 450 may optionally be used as either a 2×12 connector, or a 3×8 connector (in which case the two eight-contact leads in insertion lumens 464 and 474 do not engage the last four electrical contacts 492, and a third eight-contact lead placed within the third insertion lumen will receive the electrical signal supplied by the pulse generator assembly 104 to the open electrical contacts 492 in insertion lumens 464 and 474), in each case with all leads extending from connector block 450 in a common direction.

Other than the modular, sandwich-type assembly of connector block 450, all other features of connector block 450 are substantially identical to the features described above with respect to connector block 150 of FIGS. 1-5, including by way of non-limiting example the configuration of electrical contacts 492 within each of insertion lumens 464 and 474, and the interconnection of such electrical contacts 492 with the circuitry of pulse generator assembly 104, such that the discussion above regarding such features is equally applicable to the embodiments that comprise such modular, sandwich-type assembly of connector block 450.

Moreover, those of ordinary skill in the art will recognize that the dimensions and configuration of the various components of the adapter 500 and of connector block 450 may be varied to accommodate the use of various different leads and/or header assemblies without departing from the spirit and scope of the invention. For instance, alternative embodiments may include an adapter 500 with multiple insertion lumens of various dimensions disposed within the casing.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

I claim:

1. A connector assembly for removably attaching a plurality of leads to an implantable medical device, comprising:
    a connector block housing having a first end and a second end, said connector block housing further comprising a lower casing and an upper casing removably attached to said lower casing; and
    a first lead insertion lumen extending through said connector block housing from said first end to said second end and providing two lead points of entry through said connector block housing and into said first lead insertion lumen, said first lead insertion lumen configured to simultaneously accept leads inserted through each of said first end and said second end, said first lead insertion lumen comprising a plurality of electrical lumen contacts disposed within said first lead insertion lumen and configured to direct a electrical pulses from a pulse generator assembly to leads positioned within said first lead insertion lumen, and
    wherein said first lead insertion lumen is reconfigurable to, in a first instance, direct electrical pulses to only first and second leads having first and second numbers of electrical lead contacts, and alternatively in a second instance, to direct electrical pulses to only third and fourth leads having third and fourth numbers of electrical lead contacts that are different from said first and second numbers of electrical lead contacts.

2. The connector assembly of claim 1, said first lead insertion lumen defining a first opening within said first end of said connector block housing and a second opening within said second end of said connector block housing.

3. The connector assembly of claim 2, wherein each of said first and second openings are configured to receive a proximal end of a lead.

4. The connector assembly of claim 1, wherein said connector block housing is attached to and hermetically sealed with a pulse generator assembly housing containing a pulse generator assembly.

5. The connector assembly of claim 4, wherein said pulse generator assembly is programmable to direct an electrical pulse to at least one of said electrical lumen contacts within said lead insertion lumen.

6. The connector assembly of claim 4, wherein said pulse generator assembly is programmable to direct a first electrical pulse to a first plurality of electrical lumen contacts in contact with said first lead within said first lead insertion lumen, and to simultaneously direct a second electrical pulse to a second plurality of electrical lumen contacts in contact with said second lead within said first lead insertion lumen.

7. The connector assembly of claim 6, wherein said first plurality of electrical lumen contacts are configured to transfer said first electrical pulse to said first lead positioned within said first lead insertion lumen, and said second plurality of electrical lumen contacts are configured to simultaneously transfer said second electrical pulse to said second lead positioned within said first lead insertion lumen.

8. The connector assembly of claim 1, wherein said connector block housing is remotely connected to a pulse generator assembly housing containing a pulse generator assembly.

9. The connector assembly of claim 8, wherein said pulse generator assembly is programmable to direct an electrical pulse to at least one of said electrical lumen contacts within said lead insertion lumen.

10. The connector assembly of claim 8, wherein said pulse generator assembly is programmable to direct a first electrical pulse to a first plurality of electrical lumen contacts in contact with said first lead within said first lead insertion lumen, and to simultaneously direct a second electrical pulse to a second plurality of electrical lumen contacts in contact with said second lead within said first lead insertion lumen.

11. The connector assembly of claim 10, wherein said first plurality of electrical lumen contacts are configured to transfer said first electrical pulse to said first lead positioned within said first lead insertion lumen, and said second plurality of electrical lumen contacts are configured to simultaneously transfer said second electrical pulse to said second lead positioned within said first lead insertion lumen.

12. The connector assembly of claim 8, wherein said connector block housing is in electrical connection with said pulse generator assembly housing through at least one electrical interconnect cable.

13. The connector assembly of claim 12, wherein said electrical interconnect cable terminates at one end within said pulse generator assembly housing.

14. The connector assembly of claim 12, wherein said electrical interconnect cable terminates at one end in a lead configured for insertion into a lead connector port of said pulse generator assembly housing.

15. The connector assembly of claim 1, said connector block housing further comprising an adapter positioned between said lower casing and said upper casing and having an adapter lead insertion lumen extending into said adapter, said adapter lead insertion lumen further comprising a plurality of electrical contacts disposed within said adapter lead insertion lumen and in electrical communication with at least some of said electrical lumen contacts within said first lead insertion lumen.

16. The connector assembly of claim 15, further comprising at least one lead segment electrically communicating a portion of said electrical lumen contacts within said first lead insertion lumen with a first portion of said electrical contacts disposed within said adapter lead insertion lumen.

17. The connector assembly of claim 16, further comprising:
a second lead insertion lumen extending through said connector block housing from said first end to said second end, said second lead insertion lumen further comprising a second plurality of electrical contacts disposed within said second lead insertion lumen; and
a second lead segment electrically communicating a portion of said electrical contacts within said second lead insertion lumen with a second portion of said electrical contacts disposed within said adapter lead insertion lumen.

18. The connector assembly of claim 15, said adapter further comprising at least a first plurality of adapter contacts configured to engage with a portion of said electrical lumen contacts within said first lead insertion lumen so as to electrically communicate said portion of said electrical lumen contacts within said first lead insertion lumen with a first portion of said electrical contacts disposed within said adapter lead insertion lumen.

19. The connector assembly of claim 18, further comprising:
a second lead insertion lumen extending through said connector block housing from said first end to said second end, said second lead insertion lumen further comprising a second plurality of electrical contacts disposed within said second lead insertion lumen; and
a second plurality of adapter contacts configured to engage with a portion of said electrical contacts within said second lead insertion lumen so as to electrically communicate said portion of said electrical contacts within said second lead insertion lumen with a second portion of said electrical contacts disposed within said adapter lead insertion lumen.

20. An implantable medical device configured to receive a plurality of leads, comprising:
a pulse generator assembly housing containing a pulse generator assembly;
a connector block housing in electrical communication with said pulse generator housing and having a first end and a second end, said connector block housing further comprising a lower casing and an upper casing removably attached to said lower casing; and
at least one lead insertion lumen extending through said connector block housing from said first end to said second end and providing two points of entry through said connector block housing and into said lead insertion lumen, said lead insertion lumen configured to simultaneously accept leads inserted through each of said first end and said second end, said first lead insertion lumen comprising a plurality of electrical lumen contacts disposed within said lead insertion lumen and configured to direct electrical pulses from said pulse generator assembly to leads positioned within said lead insertion lumen, and
wherein said at least one lead insertion lumen is reconfigurable to, in a first instance, direct electrical pulses to only first and second leads having first and second numbers of electrical lead contacts, and alternatively in a second instance, to direct electrical pulses to only third and fourth leads having third and fourth numbers of electrical lead contacts that are different from said first and second numbers of electrical lead contacts.

21. The implantable medical device of claim 20, said lead insertion lumen defining a first opening within said first end of said connector block housing and a second opening within said second end of said connector block housing.

22. The implantable medical device of claim 20, wherein said connector block housing is attached to and hermetically sealed with said pulse generator assembly housing.

23. The implantable medical device of claim 22, wherein said pulse generator assembly is programmable to direct an electrical pulse to at least one of said electrical lumen contacts within said lead insertion lumen.

24. The implantable medical device of claim 22, wherein said pulse generator assembly is programmable to direct a first electrical pulse to a first plurality of electrical lumen contacts in contact with said first lead within said lead insertion lumen, and to simultaneously direct a second electrical pulse to a second plurality of electrical lumen contacts in contact with said second lead within said lead insertion lumen.

25. The implantable medical device of claim 24, wherein said first plurality of electrical lumen contacts are configured to transfer said first electrical pulse to said first lead positioned within said lead insertion lumen, and said second plurality of electrical lumen contacts are configured to simultaneously transfer said second electrical pulse to said second lead positioned within said lead insertion lumen.

26. The implantable medical device of claim 20, wherein said connector block housing is remotely connected to said pulse generator assembly housing.

27. The implantable medical device of claim 26, wherein said pulse generator assembly is programmable to direct an electrical pulse to at least one of said electrical lumen contacts within said lead insertion lumen.

28. The implantable medical device of claim 26, wherein said pulse generator assembly is programmable to direct a first electrical pulse to a first plurality of electrical lumen contacts in contact with said first lead within said lead insertion lumen, and to simultaneously direct a second electrical pulse to a second plurality of electrical lumen contacts in contact with said second lead within said lead insertion lumen.

29. The implantable medical device of claim 28, wherein said first plurality of electrical lumen contacts are configured to transfer said first electrical pulse to said first lead positioned within said lead insertion lumen, and said second plurality of electrical lumen contacts are configured to simultaneously transfer said second electrical pulse to said second lead positioned within said lead insertion lumen.

30. The implantable medical device of claim 26, wherein said connector block housing is in electrical connection with said pulse generator assembly housing through at least one electrical interconnect cable.

31. The implantable medical device of claim 30, wherein said electrical interconnect cable terminates at one end within said pulse generator assembly housing.

32. The implantable medical device of claim 30, wherein said electrical interconnect cable terminates at one end in a lead configured for insertion into a lead connector port of said pulse generator assembly housing.

33. The implantable medical device of claim 20, said connector block housing further comprising an adapter positioned between said lower casing and said upper casing and having an adapter lead insertion lumen extending into said adapter, said adapter lead insertion lumen further comprising a plurality of electrical contacts disposed within said adapter lead insertion lumen and in electrical communication with at least some of said electrical lumen contacts within said lead insertion lumen.

34. The implantable medical device of claim 33, further comprising at least one lead segment electrically communicating a portion of said electrical lumen contacts within said lead insertion lumen with a first portion of said electrical contacts disposed within said adapter lead insertion lumen.

35. The implantable medical device of claim 34, further comprising:
a second lead insertion lumen extending through said connector block housing from said first end to said second end, said second lead insertion lumen further comprising a second plurality of electrical contacts disposed within said second lead insertion lumen; and
a second lead segment electrically communicating a portion of said electrical contacts within said second lead insertion lumen with a second portion of said electrical contacts disposed within said adapter lead insertion lumen.

36. The implantable medical device of claim 33, said adapter further comprising at least a first plurality of adapter contacts configured to engage with a portion of said electrical lumen contacts within said lead insertion lumen so as to electrically communicate said portion of said electrical lumen contacts within said lead insertion lumen with a first portion of said electrical contacts disposed within said adapter lead insertion lumen.

37. The implantable medical device of claim 36, further comprising:
a second lead insertion lumen extending through said connector block housing from said first end to said second end, said second lead insertion lumen further comprising a second plurality of electrical contacts disposed within said second lead insertion lumen; and
a second plurality of adapter contacts configured to engage with a portion of said electrical contacts within said second lead insertion lumen so as to electrically communicate said portion of said electrical contacts within said second lead insertion lumen with a second portion of said electrical contacts disposed within said adapter lead insertion lumen.

38. A method for delivering an electrical pulse to a targeted location, comprising:
providing an implantable medical device configured to receive a plurality of leads, said implantable medical device comprising:
a pulse generator assembly housing containing a pulse generator assembly;
a connector block housing in electrical communication with said pulse generator housing and having a first end and a second end, said connector block housing further comprising a lower casing and an upper casing removably attached to said lower casing; and
at least one lead insertion lumen extending through said connector block housing from said first end to said second end and providing two points of entry through said connector block housing and into said lead insertion lumen, said lead insertion lumen configured to simultaneously accept leads inserted through each of said first end and said second end, said first lead insertion lumen comprising a plurality of electrical lumen contacts disposed within said lead insertion lumen and configured to direct electrical pulses from said pulse generator assembly to leads positioned within said lead insertion lumen, and
wherein said at least one lead insertion lumen is reconfigurable to, in a first instance, direct electrical pulses only to first and second leads having first and second numbers of electrical lead contacts, and alternatively in a second instance, to direct electrical pulses to only third and fourth leads having third and fourth numbers of electrical lead contacts that are different from said first and second numbers of electrical lead contacts;
implanting said implantable medical device within a patient; and
programming said implantable medical device to deliver an electrical pulse to a target location within said patient.

39. The method of claim 38, wherein said connector block housing is attached to and hermetically sealed with said pulse generator assembly housing.

40. The method of claim 39, wherein said pulse generator assembly is programmable to direct an electrical pulse to at least one electrical lumen contact within said lead insertion lumen.

41. The method of claim 40, wherein said programming step comprises programming said pulse generator assembly to direct an electrical pulse to at least one electrical lumen contact of said plurality of electrical lumen contacts within said lead insertion lumen.

42. The method of claim 39, wherein said pulse generator assembly is programmable to direct a first electrical pulse to a first plurality of electrical lumen contacts in contact with said first lead within said lead insertion lumen, and to simultaneously direct a second electrical pulse to a second plurality of electrical contacts in contact with said second lead within said lead insertion lumen.

43. The method of claim 42, wherein said first plurality of electrical lumen contacts are configured to transfer said first electrical pulse to said first lead positioned within said lead insertion lumen, and said second plurality of electrical lumen contacts are configured to simultaneously transfer said second electrical pulse to said second lead positioned within said lead insertion lumen.

44. The method of claim 43, wherein said programming step comprises programming said pulse generator assembly to direct a first electrical pulse to said first plurality of electrical lumen contacts in contact with said first lead within said lead insertion lumen, and to simultaneously direct a second electrical pulse to a second plurality of electrical lumen contacts in contact with said second lead within said lead insertion lumen.

45. The method of claim 38, wherein said connector block housing is remotely connected to said pulse generator assembly housing.

46. The method of claim 45, wherein said pulse generator assembly is programmable to direct an electrical pulse to at least one electrical lumen contact within said lead insertion lumen.

47. The method of claim 46, wherein said programming step comprises programming said pulse generator assembly to direct an electrical pulse to at least one electrical lumen contact of said plurality of electrical lumen contacts within said lead insertion lumen.

48. The method of claim 45, wherein said pulse generator assembly is programmable to direct a first electrical pulse to a first plurality of electrical lumen contacts in contact with said first lead within said lead insertion lumen, and to simultaneously direct a second electrical pulse to a second plurality of electrical lumen contacts in contact with said second lead within said lead insertion lumen.

49. The method of claim 48, wherein said programming step comprises programming said pulse generator assembly to direct a first electrical pulse to said first plurality of electrical lumen contacts in contact with said first lead within said lead insertion lumen, and to simultaneously direct a second electrical pulse to said second plurality of electrical lumen contacts in contact with said second lead within said lead insertion lumen.

50. The method of claim 49, wherein said first plurality of electrical lumen contacts are configured to transfer said first electrical pulse to said first lead positioned within said lead insertion lumen, and said second plurality of electrical lumen contacts are configured to simultaneously transfer said second electrical pulse to said second lead positioned within said lead insertion lumen.

51. The method of claim 45, wherein said connector block housing is in electrical connection with said pulse generator assembly housing through at least one electrical interconnect cable.

52. The method of claim 51, wherein said electrical interconnect cable terminates at one end within said pulse generator assembly housing.

53. The method of claim 51, wherein said electrical interconnect cable terminates at one end in a lead configured for insertion into a lead connector port of said pulse generator assembly housing.

54. The method of claim 38, wherein said connector block housing further comprises an adapter positioned between said lower casing and said upper casing and having an adapter lead insertion lumen extending into said adapter, said adapter lead insertion lumen further comprising a plurality of electrical contacts disposed within said adapter lead insertion lumen and in electrical communication with at least some of said electrical lumen contacts within said lead insertion lumen.

55. The method of claim 54, further comprising at least one lead segment electrically communicating a portion of said electrical lumen contacts within said lead insertion lumen with a first portion of said electrical contacts disposed within said adapter lead insertion lumen.

56. The method of claim 55, wherein said connector block housing further comprises:
   a second lead insertion lumen extending through said connector block housing from said first end to said second end, said second lead insertion lumen further comprising a second plurality of electrical contacts disposed within said second lead insertion lumen; and
   a second lead segment electrically communicating a portion of said electrical contacts within said second lead insertion lumen with a second portion of said electrical contacts disposed within said adapter lead insertion lumen.

57. The method of claim 55, wherein said adapter further comprises at least a first plurality of adapter contacts configured to engage with a portion of said electrical lumen contacts within said lead insertion lumen so as to electrically communicate said portion of said electrical lumen contacts within said lead insertion lumen with a first portion of said electrical contacts disposed within said adapter lead insertion lumen.

58. The method of claim 57, wherein said connector block housing further comprises:
   a second lead insertion lumen extending through said connector block housing from said first end to said second end, said second lead insertion lumen further comprising a second plurality of electrical contacts disposed within said second lead insertion lumen; and
   a second plurality of adapter contacts configured to engage with a portion of said electrical contacts within said second lead insertion lumen so as to electrically communicate said portion of said electrical contacts within said second lead insertion lumen with a second portion of said electrical contacts disposed within said adapter lead insertion lumen.

59. The method of claim 38, further comprising the step of placing distal ends of said first and second leads or of said third and fourth leads at said target location within said patient.

60. The method of claim 38, wherein said first, second, third, or fourth leads have fewer electrical lead contacts than the plurality of electrical lumen contacts in said lead insertion lumen.

61. The method of claim 38, further comprising the step of placing distal ends of said first and second leads or of said third and fourth leads at a second target location.

* * * * *